(12) United States Patent
Kunzler

(10) Patent No.: US 8,329,097 B1
(45) Date of Patent: Dec. 11, 2012

(54) STERILIZATION OF INTRAOCULAR LENSES

(75) Inventor: Jay F. Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 446 days.

(21) Appl. No.: 12/631,901

(22) Filed: Dec. 7, 2009

Related U.S. Application Data

(60) Provisional application No. 61/146,445, filed on Jan. 22, 2009.

(51) Int. Cl.
*A61L 2/00* (2006.01)
*B29D 11/00* (2006.01)
(52) U.S. Cl. .......................... 422/28; 264/2.6
(58) Field of Classification Search ............... 422/28; 264/2.6
See application file for complete search history.

(56) References Cited

U.S. PATENT DOCUMENTS

| 2004/0054026 | A1* | 3/2004 | Kunzler et al. | 523/106 |
| 2007/0282057 | A1* | 12/2007 | Mentak et al. | 524/556 |

FOREIGN PATENT DOCUMENTS

| WO | WO 03074093 A2 * 9/2003 |

\* cited by examiner

*Primary Examiner* — Kevin Joyner
(74) *Attorney, Agent, or Firm* — Joseph Barrera

(57) ABSTRACT

A packaged, sterilized intraocular lens prepared by a process comprising providing a hydrophobic acrylic, or low water acrylic, intraocular lens and positioning the acrylic lens in a lens enclosure with an aqueous solution to provide a lens package. The lens package is then heated to a temperature sufficient for sterilization, however, the heating of the lens package must begin before the acrylic lens reaches an equilibrated, hydrated state following contact of the lens with the aqueous solution. The resulting sterilized acrylic intraocular lens will have less than sixty percent of total volume of disc-like features, or less than forty percent of total volume of water vacuoles, after 60 days following sterilization compared to an acrylic lens of the same composition, which was sterilized under the same conditions, but in an equilibrated, hydrated state.

10 Claims, No Drawings

STERILIZATION OF INTRAOCULAR LENSES

CROSS REFERENCE

This application claims the benefit of Provisional Patent Application No. 61/146,445 filed Jan. 22, 2009, which is incorporated by reference herein.

FIELD OF THE INVENTION

The invention relates to intraocular lenses (IOLs) and methods of sterilizing IOLs. In particular, the invention relates to hydrophobic, acrylic IOLs or low water content, acrylic IOLs and methods of sterilizing such IOLs.

BACKGROUND OF THE INVENTION

Since the 1940s IOLs have been utilized as replacements for diseased or damaged natural ocular lenses. In most cases, an IOL is implanted within an eye at the time of surgically removing the diseased or damaged natural lens, such as for example, in the case of cataracts. For decades, the preferred material for fabricating IOLs was poly(methyl methacrylate), which is a rigid, glassy polymer.

As the technology in IOL materials progressed, softer, more flexible IOLs have gained acceptance because of their ability to be compressed, folded, rolled or otherwise deformed. As a result, the IOLs can be deformed prior to insertion of the lens through an incision in the cornea and into the eye. Once inserted, the IOL is carefully unfolded by the surgeon and the lens returns to its original pre-deformed shape. These softer IOLs can be inserted into an incision of less than 3.0 mm, whereas the earlier, more rigid IOLs required an incision size of 5 to 7.0 mm, i.e., an incision size slightly larger than the diameter of the optic portion of the IOL. Since larger incisions lead to an increased incidence of postoperative complications, the softer, more flexible IOLs are typically preferred by ocular surgeons.

The refractive power of a lens is a function of its shape and the refractive index of the material of which it is made. Accordingly, a lens made from a material having a higher refractive index can be thinner and provide the same refractive power as a lens made from a material having a relatively lower refractive index. For IOLs designed to be rolled or folded for insertion through a small incision, a lens of thinner cross section is inherently more flexible and can be rolled or folded to a smaller cross section.

In general, the materials of current commercial IOLs fall into one of three general categories: silicones, low-water hydrophilic acrylics and hydrophobic acrylics. Hydrophobic acrylic materials with a relatively low glass transition temperature (Tg ° C.) possess important material characteristics—they typically have a high refractive index and unfold with a greater degree of control. Low Tg, hydrophobic acrylic materials contain little or no water at the point of manufacture, however they do absorb small amounts of water over time if stored in an aqueous medium or following ocular insertion. The absorbed water often leads to pockets of water or vacuoles within the polymeric matrix, which leads to a reduction in the visual quality of the lens. Low Tg, hydrophobic acrylic materials also are known to develop disc-like features, which also lead to a reduction in the visual quality of the lens. The use of low water, hydrophilic acrylics minimizes the formation of these disc-like features and vacuoles.

Accordingly, there is an interest to develop a manufacturing process that minimizes the formation of the disc-like features and vacuoles in hydrophobic acrylic and low water, hydrophilic acrylic IOLs.

SUMMARY OF THE INVENTION

The invention is directed to a packaged, sterilized intraocular lens prepared by a process comprising providing a hydrophobic acrylic, or low water acrylic, intraocular lens and positioning the acrylic lens in a lens enclosure with an aqueous solution to provide a lens package. The lens package is then heated to a temperature sufficient for sterilization, however, the heating of the lens package must begin before the acrylic lens reaches an equilibrated, hydrated state following contact of the lens with the aqueous solution. The resulting sterilized acrylic intraocular lens will have less than sixty percent of total volume of disc-like features after 60 days following sterilization compared to an acrylic lens of the same composition, which was sterilized under the same conditions, but in an equilibrated, hydrated state.

The invention is also directed to a packaged, sterilized intraocular lens prepared by a process comprising providing a hydrophobic acrylic, or low water acrylic, intraocular lens and positioning the acrylic lens in a lens enclosure with an aqueous solution to provide a lens package. The lens package is then heated to a temperature sufficient for sterilization, however, the heating of the lens package must begin before the acrylic lens reaches an equilibrated, hydrated state following contact of the lens with the aqueous solution. The resulting sterilized acrylic intraocular lens will have less than forty percent of total volume of water vacuoles after 60 days following sterilization compared to an acrylic lens of the same composition, which was sterilized under the same conditions, but in an equilibrated, hydrated state.

DETAILED DESCRIPTION OF THE INVENTION

The described process for hydrophobic acrylic, or low water acrylic, intraocular lenses (IOLs) minimizes the total volume of disc-like features that are observed over time, that is, at 60 days following sterilization in an aqueous solution. One of ordinary skill in the art would recognize the disc-like features as "Frisbee-like" discs of varying size and orientation distributed throughout the acrylic lens material. The formation of the unwanted disc-like features leads to a reduction in visual quality of the lens.

The term "disc-like features" is recognized by one of ordinary skill in the art of developing polymeric, optical materials as those visible features that develop in some optical materials, particularly, hydrophobic acrylic materials, following a heat treatment, e.g., sterilization, in an aqueous environment. The disc-like features, which tend to be randomly distributed throughout the material, are visible to the eye with a microscope. Without being limited to a particular theory, Applicants suspect that the disc-like features are the result of a phase transition in the material caused by the stress of the heat treatment and the aqueous environment.

Applicants have developed a specific sterilization process to minimize the formation of disc-like features in sterilized hydrophobic acrylic, or low water acrylic, IOLs. In nearly every processing lot the described sterilization process provided sterilized IOLs with less than sixty percent, and in many cases less than thirty percent, and in most cases less than ten percent, of total volume of disc-like features after 60 days following sterilization compared to an acrylic IOL of the same composition that was sterilized under the same conditions, but in an equilibrated, hydrated form. In fact, in nearly all of the studies conducted to date, the described and claimed sterilization process completely eliminated the formation of discostic stress features in sterilized hydrophobic acrylic, or low water acrylic, IOLs. Moreover, the acrylic lenses remain free of the disc-like features indefinitely.

The described process for hydrophobic acrylic, or low water acrylic, intraocular lenses (IOLs) also minimizes the total volume of water vacuoles that are observed over time, that is, at 60 days following sterilization in an aqueous solution. One of ordinary skill in the art would recognize the water vacuoles as micro-bubbles of varying size distributed throughout the hydrophobic acrylic lens material. Applicants believe that the water vacuoles form as small amounts of water become entrapped within the lens material. To reduce the degree of surface tension between the aqueous water interface and the hydrophobic material micro-bubbles form. The formation of the unwanted water vacuoles leads to a reduction in visual quality of the lens.

Applicants' sterilization process minimizes the formation of water vacuoles in sterilized hydrophobic acrylic, or low water acrylic, IOLs. In nearly every processing lot the described sterilization process provided sterilized IOLs with less than forty percent, and in most cases less than thirty percent, of total volume of water vacuoles 60 days following sterilization compared to an acrylic IOL of the same composition that was sterilized under the same conditions, but in an equilibrated, hydrated form.

Accordingly, the invention is directed to a sterilized intraocular lens prepared by a process comprising providing a hydrophobic acrylic, or low water content acrylic, intraocular lens and positioning the acrylic lens in a lens enclosure with an aqueous solution to provide a lens package. The lens package is then heated to a temperature sufficient for sterilization, however, the heating of the lens package must begin before the acrylic lens reaches an equilibrated, hydrated state following contact of the lens with the aqueous solution. The resulting sterilized intraocular lens will have less than sixty percent, preferably less than thirty percent, more preferably less than ten percent, total volume of discotic features, or less than forty percent, and in most cases less than thirty percent, of total volume of water vacuoles, 60 days following sterilization than a lens of the same composition that was sterilized under the same conditions, but in an equilibrated, hydrated state.

As described in greater detail, the IOLs sterilized by the described procedure are only those characterized by those of ordinary skill in the art as hydrophobic acrylic, or low water content acrylic, IOLs. The term "hydrophobic acrylic" means that in an equilibrated, hydrated state the lens will comprise less than 10% by weight water. See, polymeric lens materials described under the sub-heading, "Hydrophobic Acrylic IOLs". In one embodiment, the hydrophobic acrylic intraocular lens sterilized by the described process can include silicon monomeric units. See, polymeric lens materials described under the sub-heading, "Hydrophobic Silicone IOLs".

The term "low water content acrylic" is a (meth)acrylate material that in an equilibrated, hydrated state the lens will comprise from 5% to 15% by weight water. See, polymeric lens materials described under the sub-heading, "Low Water Content Acrylic IOLs".

One of ordinary skill in the art would understand that the term "equilibrated hydrated state" means that a lens in contact with an aqueous solution is allowed sufficient time for the water to become absorbed into the lens and reach a state of equilibrium such that the lens is not capable of absorbing additional amounts of water from the solution. The time it takes for any one hydrophobic lens to reach an equilibrated hydrated state is determined by carefully weighing the lens disposed in the solution at different time intervals and recording the time it takes for the lens to reach a substantially constant weight.

In one embodiment, the heating of the lens for sterilization begins before the lens reaches a 50% hydrated state, that is, the lens has absorbed less than 50% by weight of the water for a given aqueous solution compared to the total amount of water the lens would absorb using the same aqueous solution but allowing the lens to reach its equilibrated hydrated state. Similarly, in another embodiment, the heating of the lens for sterilization begins before the lens reaches a 25% hydrated state.

In one embodiment, the heating of the lens package begins within six hours of contacting the lens with the aqueous solution with the lens package at room temperature. In another embodiment, the heating of the lens package should begin within two hours of contacting the lens with the aqueous solution with the lens package at room temperature.

Typically, an intraocular lens is manufactured in one of two ways. One method involves casting the IOL in a lens mold of set dimensions to provide a lens with a predetermined optical power. The lens is then removed from the mold and extracted with water, an organic solvent or a mixed aqueous organic solvent, e.g., water/hexanol, to remove reaction side products, e.g., oligomers, or unreacted monomer. The lens can further be refined, e.g., edging or polishing the lens within set quality specifications. The refined lens is then placed in a buffered saline solution and the lens material reaches an equilibrated hydrated state prior to sterilization. The sterilization process will generally include the sealing of the lens package prior to sterilization.

The second method involves casting the polymeric material in the form of a rod. The rod is sliced to provide polymeric discs or "buttons", which are then machined to the desired shaped IOL. The buttons or machined IOL is then extracted to remove reaction impurities. Again, the refined lens is placed in the buffered saline solution and the lens material reaches an equilibrated hydrated state prior to sterilization.

As stated, each of the above manufacturing methods will often include an extraction step. Accordingly, the described process can include extracting a polymerized hydrophobic intraocular lens with a low-expanding organic solvent to remove unwanted polymerization products or non-reacted monomer from the polymerized lens.

Following the extraction process, the hydrophobic IOL is preferably not placed in buffered saline, but is instead, dried under vacuum at temperatures from 40° C. to 110° C. for at least thirty minutes. The IOL is maintained in a dry state until the sterilization process.

It is to be understood, however, that one of ordinary skill in the art of developing or manufacturing optical polymeric lenses understands that an extraction step is optional, and materials and processes can be developed that would exclude such an extraction step.

Hydrophobic Acrylic IOLs

Hydrophobic acrylic IOLs are essentially a copolymer comprised of at least three monomeric components. The first monomeric component, which is preferably present in the copolymer from about 30% to about 85% by weight, is best described by its corresponding homopolymer. The homopolymer of the first monomeric component will have a refractive index of at least about 1.50, preferably at least about 1.52 or about 1.54, and preferably have a substantial degree of rigidity. Likewise, the second monomeric component, which is preferably present in the copolymer from 5% to about 30% by weight, is best described by its corresponding homopolymer. The homopolymer of the second monomeric component will have a glass transition temperature from about −100° C. to about 60° C. The first and second monomeric components preferably constitute at least about 80%, more preferably at least about 90%, by weight of the copolymer. Moreover, it can be advantages to use a first and a second monomeric components that have similar reactivity ratios such that a more homogeneous copolymer matrix is prepared from the two monomeric components.

As used herein, the term "homopolymer" refers to a polymer which is derived substantially completely from the monomeric component in question. Thus, such homopolymer includes as the primary, preferably sole, monomeric component, the monomeric component in question. Minor amounts of catalysts, initiators and the like can be included, as is conventionally the case, in order to facilitate the formation of the homopolymer.

The third monomeric component of the copolymer is a crosslinking component, which can form crosslinks with each of the first and second monomeric components. The crosslinking monomeric component is preferably multifunctional and can chemically react with both the first and second monomeric components. The crosslinking component is present in the copolymers in an amount effective to facilitate returning a deformed IOL made from the composition to its original shape, for example, in a reasonable period of time, following insertion of a folded IOL in the eye.

It is to be understood by those of ordinary skill that the first, second and third monomeric components should be such as to provide a copolymer that is compatible for use in the eye, is optically clear and is otherwise suitable for use as an IOL material. It is also understood that each monomeric component includes at least one polymerizable functional group containing a carbon-carbon double bond.

The monomeric components, particularly if they have an aromatic moiety can be non-substituted or substituted. The substituents can include one or more elements, such as oxygen, nitrogen, carbon, hydrogen, halogen, sulfur, phosphorus, and the like and mixtures and combinations thereof.

Particularly useful first monomeric components include styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, 2,3-dibromopropyl acrylate and any one mixture thereof.

In one embodiment, the first monomeric component is characterized as including one or more aryl-containing groups, which is believed to provide the copolymer with a relative high refractive index. The selection of an appropriate first monomeric component, and the amount of such component used to form the copolymer, can effectively control the refractive index of the copolymer. Accordingly, it is not necessary for the other monomeric components to appreciably contribute to the high refractive index of the materials. This "single refractive index control" is very effective in achieving high refractive index copolymers, and allows flexibility in selecting the other monomeric component or components so that copolymers with advantageous properties, other than refractive index, for example, copolymers formable into IOLs which can be effectively deformed (for insertion) at room temperature, can be obtained.

Particularly useful second monomeric components include n-butyl acrylate, n-hexyl acrylate, 2-ethylhexyl acrylate, 2-ethoxyethyl acrylate, 2,3-dibromopropyl acrylate, n-1,1-dihydroperfluorobutyl acrylate and mixtures thereof.

The crosslinking monomeric component is often present in a minor amount relative to the amounts of the first and second monomeric components. Typically, the crosslinking component is present in the copolymer in an amount of less than about 1% by weight of the copolymer. The crosslinking monomeric component is often selected from multifunctional crosslink component, preferably able to chemically react with at least one functional group of each of the first monomeric component and the second monomeric component. The crosslinking monomeric component is chosen to have a reactivity ratio similar to both the first monomeric component and the second monomeric component. Examples of useful crosslinking monomeric components include ethylene glycol dimethacrylate, propylene glycol dimethacrylate, ethylene glycol diacrylate and the like and any one mixture thereof.

In some of the more preferred embodiments, the first monomeric component is of formula (I)

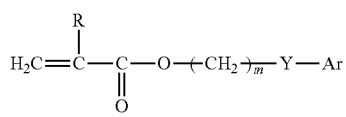

I wherein: X is H or CH$_3$; m is 0-6; Y is nothing, O, S, or NR with R is H, C$_{1-4}$alkyl, iso-OC$_3$H$_7$, phenyl or benzyl;

Ar is any aromatic ring, such as benzene, which can be unsubstituted or substituted, including CH$_3$, C$_{1-4}$alkyl, C$_{1-3}$oxyalkyl, phenyl and benzyl. The aromatic substituents also include the aromatic substituents listed with formula (I) above.

Suitable monomers of formula II include 2-ethylphenoxy acrylate, 2-ethylphenoxy acrylate, 2-ethylthiophenyl acrylate, 2-ethylthiophenyl acrylate, 3-phenylpropyl acrylate, 2-ethylaminophenyl acrylate, phenyl acrylate, benzyl acrylate, 2-phenylethyl acrylate, 4-phenylbutyl crylate, 4-methylphenyl acrylate, 4-methylbenzyl acrylate, 2-2-methylphenylethyl acrylate, 2-3-methylphenylethyl acrylate, 2-4-methylphenylethyl acrylate, 2-(4-propylphenyl)ethyl acrylate, 2-(4-(1-methylethyl)phenyl)ethyl acrylate, 2-(4-methoxyphenyl)ethyl acrylate, 2-(4-cyclohexylphenyl)ethyl acrylate, 2-(2-chlorophenyl)ethyl acrylate, 2-(3-chlorophenyl)ethyl acrylate, 2-(4-chlorophenyl)ethyl acrylate, 2-(4-bromophenyl)ethyl acrylate, 2-(3-phenylphenyl)ethyl acrylate, 2-(4-phenylphenyl)ethyl acrylate), 2-(4-benzylphenyl) ethyl acrylate including for each listed the corresponding methacrylate.

It will be understood by those skilled in the art that among polymers of acrylic esters, those made from acrylate ester monomers tend to have lower glass transition temperatures and to be more flexible than polymers of methacrylate esters. Accordingly, the aryl acrylate/methacrylate copolymers used in the IOL's of this invention will generally comprise a greater mole percent of acrylate ester residues than of methacrylate ester residues. It is preferred that the aryl acrylate monomers constitute from about 60 mole percent to about 95 mole percent of the polymer, while the aryl methacrylate monomers constitute from about 5 mole percent to about 40 mole percent of the polymer.

The appropriate selection of monomeric components and their respective amounts in the copolymer should provide a polymeric material having a glass transition temperature not greater than about 60° C., preferably not greater than 40° C. It is preferred to use polymers having a glass transition temperature somewhat below normal body temperature and no greater than normal room temperature, e.g., about 20° C. to 25° C., in order that the lenses can be rolled or folded conveniently at room temperature.

One preferred copolymer material for an IOL comprises about 60-70 mole percent 2-phenylethyl acrylate (PEA); and about 30-40 mole percent 2-phenylethyl methacrylate (PEMA). A homopolymer of the PEA has an optical refractive index of about 1.56, and are relatively rigid. For example, while a one centimeter diameter rod of such a homopolymer is somewhat rubbery, if this rod is bent into a U-shape cracks will likely form at the base of the U. A homopolymer of PEMA has a glass transition temperature of −58° C. The resulting copolymer has a refractive index of 1.537. A one centimeter diameter rod of this copolymer can be folded 180° with no observed cracking and return to its original shape within a few seconds.

The following hydrophobic acrylic formulation is blended, purged with nitrogen for 3 minutes and cured into a crosslinked copolymer.

89 wt. % 2-phenoxyethyl acrylate,
9.5 wt. % n-hexyl acrylate,
9.0 wt. % ethylene glycol dimethacrylate,
0.35 wt. % 2,2'-azobis(2,4-dimethylpentanenitrile),
0.05 wt. % 2,2'-azobis(2-methylbutanenitrile) and
1.5 wt. % x-monomer (need chemical name).

The cure temperature cycle used is as follows: heat from 250° C. to 500° C. in 30 minutes; maintain at 500° C. for 5 hours; heat from 500° C. to 900° C. in 4 hours; maintain at 900° C. for 1 hour; and cool from 900° C. to 250° C. in 6 hours. The post-cure temperature cycle used is as follows: heat from 250° C. to 1200° C. in 3 hours; maintain at 1200° C. for 2 hours; and cool from 1200° C. to 25° C. in 3 hours.

Another hydrophobic acrylic formulation is blended, purged with nitrogen for 3 minutes and cured into a crosslinked copolymer. The cure and post-cure heating and cooling regimens are the same as those described above.

88.5 wt. % 2-phenoxyethyl acrylate,
5 wt. % n-hexyl acrylate,
4 wt. % N-vinyl pyrrolidone
0.35.0 wt. % ethylene glycol dimethacrylate,
0.05 wt. % 2,2'-azobis(2,4-dimethylpentanenitrile),
0.05 wt. % 2,2'-azobis(2-methylbutanenitrile) and
1.5 wt. % x-monomer (see chemical structure below).

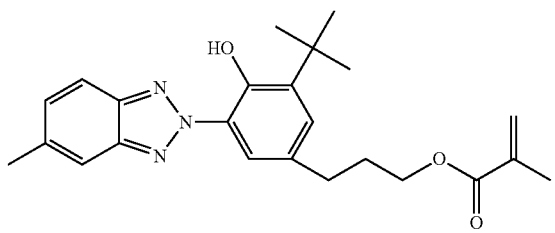

Another hydrophobic acrylic formulation is comprising 90 mole percent 2-phenylethyl acrylate (PEA), 5 mole percent, 2-phenylethyl methacrylate (PEMA), 5 mole percent 1-6 hexanediol dimethacrylate (HDDMA), and 0.1 percent by weight of bis-(4-t-butylcyclohexyl) peroxydicarbonate is degassed and transferred into either an IOL mold and or a film mold made of two glass plates with one layer of a polyethylene terephthalate film on each facing side, with the plates being separated by a silicone gasket of 0.8 mm thickness. Both molds are designed so that there would be no differential pressure buildup between the inside and the outside of the mold during the polymerization. The mold is completely filled by injecting the mixture, e.g., by means of a syringe, into a filling port until the mold was filled and excess monomer mixture was discharged through an exit vent.

The filled molds are heated in an inert environment for 15 hours at 50° C. At the end of the polymerization period, the molds are opened and the cured intraocular lens and sheet of polymer are removed. The intraocular lens is observed to be soft, foldable, and of high refractive index (approximately 1.55) with a glass transition temperature of approximately 12° C.

Additional IOLs can be made using the above procedure but varying the proportions of the monomeric components. The formulations and glass transition temperature (Tg) of the lenses are listed in Table 1.

TABLE 1

| PEA | PEMA | POEA | HDDMA | BDDA | Tg ° C. |
|-----|------|------|-------|------|---------|
| 88  | 10   | —    | 2     | —    | 10      |
| 78  | 20   | —    | 2     | —    | 15      |
| 65  | 30   | —    | —     | 3.2  | 17      |
| 80  | 15   | —    | —     | 3.2  | 11      |
| —   | 30   | 65   | —     | 3.2  | —       |

BDDA is butanedioldiacrylate crosslink agent
POEA is 2-phenoxy acrylate

Low Water Content Acrylic IOLs

The present invention relates to an acrylic IOL having a water content from 5% to 15% by weight water in its equilibrated hydrated state whereas many current hydrophobic acrylic IOLs on the market have an equilibrated hydrated water content of less than 4.5% by weight. One advantage to the low water content acrylic IOLs is that one can observe a reduction in the amount of water vacoule formation, often referred to in the art as 'glistenings" while achieving particularly desirable physical properties.

Like the hydrophobic acrylic IOL materials one typically would select a first monomeric component, a second monomeric component and a third (crosslinking) component as previously described. The difference between the two materials comes with the addition of a sufficient amount of a fourth monomeric component. This fourth component is present in the acrylic polymer from about 2% to about 20% by weight. This fourth component is generally referred to by those in the art as a hydrophilic monomer. Also, the presence of hydrophilic monomer can often reduce the tackiness of the copolymer relative to a substantially identical copolymer without the fourth hydrophilic monomeric component. In addition, the presence of a hydrophilic monomeric component can help to minimize the formation of the described water vacuoles.

As used herein, the term "hydrophilic monomeric component" refers to compounds which produce hydrogel-forming homopolymers, that is, homopolymers which in an equilibrated, hydrated state comprise at least about 20% by weight water based, and which physically swell as a result of its water uptake. Specific examples of useful hydrophilic monomeric components include N-vinyl pyrrolidone; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

Alternatively, the fourth monomeric component is an aromatic-based monomer of formula II G-D-Ar                                                    (II)

wherein Ar is a $C_6$-$C_{14}$ aromatic group having at least a hydrophilic substituent, D is a divalent linking group, and G is a reactive functional group. In one embodiment, Ar is a phenyl or a fused aromatic ring with a substituent selected from the group consisting of carboxy, alcohols (including monohydric and polyhydric alcohols), and combinations thereof. Exemplary substituents on the aromatic group include —COOH, —$CH_2$—$CH_2OH$, —(CHOH)$_2$—$CH_2OH$, —$CH_2$—CHOH—$CH_2OH$, poly(alkylene glycol) such as poly(ethylene glycol) having a formula of —(O$CH_2CH_2$)$_n$OH, wherein n is an integer from $1 \leq n \leq 20$, and combinations thereof.

In still another embodiment, Ar is a phenyl or a fused aromatic ring with a substituent selected from the group consisting of carboxamide, dialkyl-substituted carboxamide, amino, alkanolamino, sulfonate, phosphonate, sulfate, phosphate, ureido, substituted sugars, and combinations thereof.

G is a reactive functional group selected from the group consisting of vinyl, allyl, acryloyl, acryloyloxy, methacryloyl, methacryloyloxy, epoxide, isocyanate, isothiocyanate, amino, hydroxyl, mercapto, anhydride, carboxylic, fumaryl, styryl, and combinations thereof. Preferably, G is selected from the group consisting of vinyl, styryl, acryloyloxy, and methacryloyloxy.

D is a divalent group selected from the group consisting of straight or branched $C_1$-$C_{10}$ hydrocarbons, cyclic $C_3$-$C_{10}$ hydrocarbons, and alkyloxy substituents. Preferably, D is a saturated straight $C_1$-$C_{10}$ hydrocarbon divalent group.

In one embodiment, an aromatic-based monomer has a formula (i)

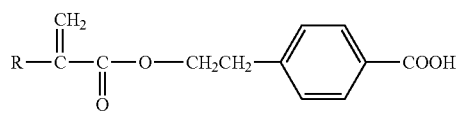

(i)

wherein R is either hydrogen or $CH_3$.

In another embodiment, an aromatic-based monomer has a formula (ii)

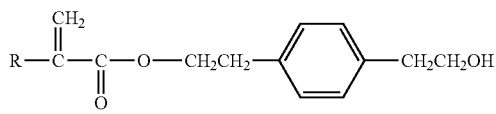

(ii)

wherein R is hydrogen or $CH_3$.

In still another embodiment, an aromatic-based monomer has a formula (iii)

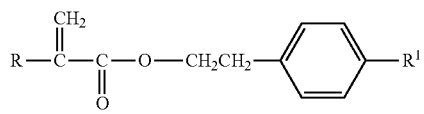

(iii)

wherein $R^1$ is —C(O)O—$NH_2$ or —C(O)—N($CH_3$)$_2$.

Low water content acrylic IOLs were produced from formulations in n-hexanol based on the polymerization of the copolymer PPA/DMA/APDMS (3-phenylpropyl acrylate-co-N,N-dimethylacrylamide-co-3 acryloyloxypropyldiphe-nylmethylsilane) in 20 w/v. % hexanol with the listed amount of crosslink agent, ethyleneglycol dimethacrylate, set forth below in Table 2. All formulations contain 0.5 percent by weight Irgacure™ 819 (Ciba-Geigy, Basel, Switzerland) and no UV blocker. The physical and mechanical properties of each of the acrylic materials are also reported.

Alternatively, the fourth monomeric component is an aromatic-based monomer of formula III

wherein Ar is a substituted or non-substituted $C_6$-$C_{14}$ aromatic group, D is a divalent, hydrophilic linking group, and G is a reactive functional group. In one embodiment, Ar is a phenyl or a fused aromatic ring. The linking group D includes one or more substituent selected from the group consisting of carboxy, alcohols (including monohydric and polyhydric alcohols), and combinations thereof. Exemplary substituents on the include —COOH, —$CH_2$—$CH_2OH$, —(CHOH)$_2$—$CH_2OH$, —$CH_2$—CHOH—$CH_2OH$, poly(alkylene glycol) such as poly(ethylene glycol) having a formula of —(O$CH_2CH_2$)$_n$O—, wherein n is an integer from $1 \leq n \leq 20$, and combinations thereof.

In one embodiment, a monomer of formula (III) is represented as follows

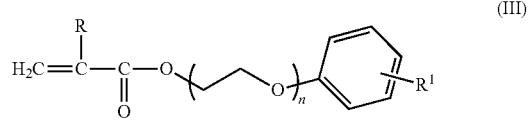

(III)

wherein R is either hydrogen or $CH_3$, $R^1$ is hydrogen, $C_3$-$C_{12}$ alkyl with optional oxygen functionality such as carboxy and alcohols (including monohydric and polyhydric alcohols).

TABLE 2

| Formulation (wt. %) | R.I. | Mod (g/mm²) | Tear (g/mm) | % Elong. | wt. % H₂O |
|---|---|---|---|---|---|
| (75/25/0, 20/1) | 1.5349 | | | | 5.1 |
| (75/25/0, 20/2) | 1.5364 | 55 | 24 | 197 | 6.5 |
| (75/25/0, 20/3) | | | | | 5.0 |
| (65/25/10, 20/2) | 1.5442 | 81 | 54 | 228 | 5 |
| (65/25/10, 20/3) | 1.5448 | 143 | 57 | 178 | 5.7 |
| (55/25/20, 20/1) | 1.5409 | 94 | 79 | 332 | 5.5 |
| (55/25/20, 20/2) | 1.5429 | 141 | 77 | 232 | 4.8 |
| (55/25/20, 20/3) | 1.5422 | 196 | 83 | 184 | 5 |

Low water content acrylic IOLs were produced from formulations in n-hexanol based on the polymerization of the copolymer PPA/DMA/MMA or (3-phenylpropyl acrylate-co-N,N-dimethylacrylamide-co-methyl methacrylate) set forth below in Table 3. All formulations contain a crosslink agent, ethyleneglycol dimethacrylate, at 3.0 wt. %, 0.5 wt. % Irgacure™ 819 (Ciba-Geigy, Basel, Switzerland) and no UV blocker. The physical and mechanical properties of each of the acrylic materials are also reported.

TABLE 3

| Formulation | R.I. | Mod (g/mm²) | Tear (g/mm) | % Elong. | % H₂O |
|---|---|---|---|---|---|
| 65/30/35 | 1.5108 | 290 | 127 | 254 | 11.3 |
| 65/0/35 | 1.5252 | 81 | 16 | 89 | 6.7 |

TABLE 3-continued

| Formulation | R.I. | Mod (g/mm$^2$) | Tear (g/mm) | % Elong. | % H$_2$O |
|---|---|---|---|---|---|
| 6510/35 | 1.5164 | 93 | 36 | 137 | 10.1 |
| 6520/35 | 1.517 | 161 | 72 | 183 | 10.5 |

Hydrophobic Silicone IOLs

The hydrophobic IOLs can be prepared from a reinforced cross-linked silicone prepolymer which includes a polymer containing 12 to 18 mol percent of aryl substituted siloxane units of the formula $R^4R^5$—SiO. In the formula, $R^4$ and $R^5$ are the same or different and represent phenyl, mono-lower alkyl substituted phenyl groups, or di-lower alkyl substituted phenyl groups. Preferably both R4 and R5 are phenyl.

The silicone prepolymer can have end blockers containing siloxane units of the formula $R^1R^2R^3$—SiO$_5$ wherein $R^1$ and $R^2$ are alkyl, aryl or substituted alkyl or substituted aryl groups, and $R^1$ and $R^2$ can be the same or different. The $R^3$ group of the end blocking siloxane units is an alkenyl group. Preferably, the end blocker is a dimethylvinyl siloxane unit or a methacrylate. The balance of the silicone IOL can comprise dialkyl siloxane units of the formula $R^6R^7$—SiO wherein $R^6$ and $R^7$ are the same or different from and are methyl or ethyl groups, and the elastomer has a degree of polymerization from 100 to 2000. Preferably, $R^6$ and $R^7$ are both methyl, and the degree of polymerization is approximately 250.

A trimethyl silyl treated silica reinforcer finely dispersed in the elastomer, present in a weight ratio of approximately 15 to 45 parts of the reinforcer to 100 parts of the silicone prepolymer, to provide a lens material with a sufficient modulus value suitable for an IOL. Preferably, there is approximately 27 parts of reinforcer to 100 parts of the prepolymer.

In one embodiment, the hydrophobic silicone IOL is a silicone material described in U.S. Pat. No. 5,236,970. In another embodiment, A silicone prepolymer that ie either monofunctional or difunctional can be used in combination with hydrophobic acrylic monomers. Such materials are described in U.S. Pat. Nos. 7,169,874; 7,009,023; 6,908,978, each of which is assigned to Bausch & Lomb Incorporated, Rochester, N.Y.

The lenses must exhibit sufficient strength to allow them to be folded without fracturing. Polymers exhibiting an elongation of at least 150% are preferred. Most preferably, the polymers exhibit an elongation of at least 200%. Lenses made from polymers which break at less than 150% elongation may not endure the distortion which necessarily occurs when they are rolled or folded to a dimension small enough to pass through a small incision.

The copolymers are produced using conventional polymerization techniques. For example, the monomers can be blended together and heated to an elevated temperature to facilitate the polymerization reaction. Catalysts and/or initiators, for example, selected from materials well known for such use in the polymerization art, may be included in the monomer mix in order to promote, and/or increase the rate of, the polymerization reaction. Examples of such initiators include 2,2'-azobis(2,4-dimethylpentanenitrile), 2,2'-azobis (2-methylpropanenitrile), 2,2'-azobis(2-methylbutanenitrile), platinum-based initiators, peroxides such as benzoyl peroxide, UV initiators such as diethoxyacetophenone, and the like and mixtures thereof. In addition, effective amounts of ultraviolet light absorbing monomeric components, such as functional benzotriazole and benzophenone derivatives, may be included in the precursor monomer mix. Such UV light absorbing monomeric components are polymerized into the final copolymer to provide the final copolymer with effective UV light absorbing properties.

In one embodiment, the copolymers are produced by mixing together the first monomeric component and the second monomeric component (and the fourth monomeric component, if any). This mixture is well blended, deareated and heated at an elevated temperature for a sufficient period of time to form a partially polymerized viscous liquid. The times and temperatures used will of course depend in-part on the monomeric components selected and is within the skill of one of ordinary skill in the art. To the viscous liquid is added the crosslinking monomeric component and catalyst and/or an initiator. Alternately, all the monomeric components and catalyst and/or initiator can be combined or mixed together.

The viscous liquid, or monomeric mixture, is well blended, deareated and poured into a mold. The liquid or mixture is allowed to cure. After curing (and post-curing), the mold is disassembled and the molded optic recovered.

The following non-limiting examples illustrate certain aspects of the present invention.

Example 1

To 65 parts of 3-phenylpropyl acrylate (PPA) was added 25 parts of N,N-dimethylacrylamide (DMA), 20 parts of hexanol, 10 parts of methyl methacrylate (MMA), 3 parts of ethyleneglycol dimethacrylate (EG) as crosslinker, 0.5% by weight Irgacure®819 as UV photoinitator and 0.25 wt % of a commercial triazole UV blocker (PQ 15014 from Aldrich Chemical). The clear solution was sandwiched between two silyated glass plates using metal gaskets and exposed to visible light for 2 hours. The resultant film (about 0.15 mm in thickness) was released from the plates and extracted in isopropanol (IPA) for 4 hours. The extracted film was air-dried and then vacuum dried at ambient temperature (30 mm Hg) to remove any remaining IPA. Two discs were cut from the film. One disc was placed in borate buffered saline (BBS) and autoclaved (Market Forge Sterilmatic) within 30 minutes after contact with the BBS, and heat sterilized for 30 minutes at 122° C. and 15 psi. The heat sterilized disc slowly cooled to ambient temperature and stored in the BBS. No disc-like features (opaque discs) or vacuoles were observed following sterilization or up to two weeks following sterilization.

The Example 1 process was repeated and provided near identical results—no disc-like features or vacuoles.

Comparative Example 1A (CE 1A)

The remaining disc from Example 1 was placed in the BBS for at least 15 hours (overnight). The hydrated disc was autoclaved for 30 minutes at 122° C. and 15 psi, and allowed to cool slowly to ambient temperature. Disc-like features were observed throughout the disc.

Comparative Example 1B (CE 1B)

The disc free of disc-like features or vacuoles was placed in BBS for two weeks and the autoclave step was repeated. Disc-like features were observed throughout the disc.

Examples 2 to 4

The same procedure described in Example 1 was used to make polymer films prepared from the polymer mixtures listed in Table 4A. Four discs were cut from each of the prepared polymer films. Two of the four discs were autoclaved within 30 minutes of contact with the BBS. The clarity of each of the discs is reported in Table 4B.

TABLE 4A

| Example No. | PPA | DMA | MMA | EG |
|---|---|---|---|---|
| 2 | 65 | 35 | — | 3 |
| 3 | 65 | 35 | 20 | 3 |
| 4 | 65 | 35 | 30 | 3 |

TABLE 4B

| Example No. | stress features | vacuoles |
|---|---|---|
| 2 | none | none |
| 3 | two | none |
| 4 | two | none |

Comparative Examples 2 to 4

The remaining two discs from each of Examples 2 to 4 was placed in the BBS for at least 48 hours. The hydrated discs were autoclaved for 30 minutes and allowed to cool slowly to ambient temperature. The clarity of each of the discs is reported in Table 4C.

TABLE 4C

| Example No. | stress features | vacuoles |
|---|---|---|
| CE 2 | TNC | yes |
| CE 3 | TNC | yes |
| CE 4 | TNC | yes |

TNC—to numerous to count

Examples 5 to 7

The same procedure described in Example 1 was used to make polymer films prepared from the polymer mixtures listed in Table 5A. These films do not include methyl methacrylate and are polymerixed with 0.25 wt. % UV blocker and 0.25 wt. % Irgacure®369. Four discs were cut from each of the prepared polymer films. One disc for each Example (i.e., Disc 5a, 6a and 7a) was heat sterilized following a one hour hydration time in BBS. Another disc for each Example (i.e., Disc 5b, 6b and 7b) was heat sterilized following a four hour hydration time in BBS. Another disc for each Example (i.e., Disc 5c, 6c and 7c) was heat sterilized following a six hour hydration time in BBS. Lastly, the fourth disc from each Example (i.e., Disc 5 CE, 6 CE and 7 CE) was heat sterilized following storage in BBS overnight (about 14 hours). Disc 5 CE, 6 CE and 7 CE are comparative examples and noted with CE. The clarity of each of the discs is reported in Tables 5B, 5C and 5D.

TABLE 5A

| Example No. | PPA | DMA | EG |
|---|---|---|---|
| 5 | 65 | 35 | 3 |
| 6 | 65 | 35 | 4 |
| 7 | 65 | 35 | 5 |

TABLE 5B

| Example No. | stress features | vacuoles |
|---|---|---|
| 5a | none | none |
| 5b | none | none |
| 5c | few | some |
| 5 CE | numerous | numerous |

TABLE 5C

| Example No. | stress features | vacuoles |
|---|---|---|
| 6a | none | none |
| 6b | none | none |
| 6c | none | many (center of disc) |
| 6 CE | numerous | numerous |

TABLE 5D

| Example No. | stress features | vacuoles |
|---|---|---|
| 7a | none | none |
| 7b | none | none |
| 7c | none | none |
| 7 CE | numerous | numerous |

I claim:

1. A process for sterilizing an intraocular lens, the process comprising:
   providing a hydrophobic acrylic, or low water acrylic, intraocular lens and positioning the acrylic lens in a lens enclosure with an aqueous solution; and
   heating the lens enclosure to a temperature sufficient for sterilization, wherein the heating of the lens enclosure must begin before the acrylic lens reaches an equilibrated, hydrated state following contact of the lens with the aqueous solution, said sterilized intraocular lens to have less than sixty percent of total volume of disc-like features after 60 days following sterilization compared to an acrylic lens of the same composition that was sterilized under the same conditions, but in an equilibrated, hydrated state.

2. The process of claim 1 wherein the acrylic lens comprises acrylate or methacrylate monomeric units with aromatic functionality.

3. The process of claim 1 wherein the intraocular lens comprises silicon monomeric units.

4. The process of claim 1 further comprising extracting the acrylic intraocular lens with a low-expanding organic solvent to remove unwanted polymerization products or non-reacted monomer from the polymerized lens, and drying the solvent-extracted lens under vacuum at temperatures from 40° C. to 110° C. for at least thirty minutes prior to positioning the acrylic lens in a lens enclosure.

5. The method of claim 1 wherein the providing of the acrylic intraocular lens includes drying a solvent-extracted lens under vacuum at temperatures from 40° C. to 110° C. for at least thirty minutes.

6. The method of claim 1 wherein said sterilized intraocular lens has less than thirty percent of total volume of disc-like features after 60 days following sterilization compared to the lens of the same composition that was sterilized under the same conditions, but in an equilibrated, hydrated form.

7. The method of claim 1 further comprising sealing the lens enclosure prior to heating.

8. The method of claim 1 wherein the heating of the lens enclosure begins within two hours of contacting the acrylic lens with the aqueous solution with the lens package at room temperature.

9. The method of claim 1 wherein the acrylic lens comprises acrylate or methacrylate monomeric units of formula III

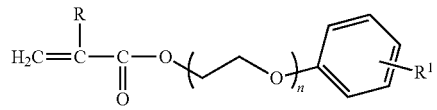
(III)

wherein R is either hydrogen or $CH_3$, $R^1$ is hydrogen, $C_3$-$C_{12}$ alkyl with optional oxygen functionality selected from carboxy and monohydric or polyhydric alcohols.

10. The method of claim 1 wherein the acrylic lens is a copolymer comprising:

a first monomeric component, present in the copolymer from 30% to 85% by weight, a homopolymer of the first monomeric component will have a refractive index of at least about 1.50; and a second monomeric component, present in the copolymer from 5% to about 30% by weight, a homopolymer of the second monomeric component will have a glass transition temperature from about −100° C. to about 60° C., wherein the first and the second monomeric components comprise at least about 80% by weight of the copolymer.

\* \* \* \* \*